United States Patent [19]
Wagnières et al.

[11] Patent Number: 6,148,227
[45] Date of Patent: Nov. 14, 2000

[54] DIAGNOSIS APPARATUS FOR THE PICTURE PROVIDING RECORDING OF FLUORESCING BIOLOGICAL TISSUE REGIONS

[75] Inventors: Georges Wagnières, Morges; Matthieu Zellweger, Lausanne; Nicolas Chauvin, Lausanne; Norbert Lange, Lausanne, all of Switzerland; Ulf Zanger, Weingarten, Germany; André Studzinski, La Tour-de-Peilz; Hubert van den Bergh, Goumoens la Ville, both of Switzerland

[73] Assignee: Richard Wolf GmbH, Knittlingen, Germany

[21] Appl. No.: 09/098,286

[22] Filed: Jun. 16, 1998

[30] Foreign Application Priority Data

Jan. 7, 1998 [DE] Germany .................. 198 00 312

[51] Int. Cl.⁷ .................................................. A61B 5/00
[52] U.S. Cl. ............................ 600/476; 600/160; 348/77
[58] Field of Search .......................... 600/476, 160, 600/473; 348/45, 46, 49, 54, 55, 60, 65, 68, 70, 71, 76, 77; 250/461.2

[56] References Cited

U.S. PATENT DOCUMENTS

| | | | |
|---|---|---|---|
| 4,532,918 | 8/1985 | Wheeler | 128/6 |
| 4,821,117 | 4/1989 | Sekiguchi . | |
| 5,134,662 | 7/1992 | Bacus et al. | 382/6 |
| 5,165,079 | 11/1992 | Schulz-Hennig | 359/634 |
| 5,225,883 | 7/1993 | Carter et al. | 356/45 |
| 5,255,087 | 10/1993 | Nakamura et al. | 358/98 |
| 5,420,628 | 5/1995 | Poulsen et al. | 348/61 |
| 5,430,476 | 7/1995 | Hafele et al. | 348/70 |
| 5,647,368 | 7/1997 | Zeng et al. | 128/655 |

FOREIGN PATENT DOCUMENTS

| | | |
|---|---|---|
| 0 512 965 A1 | 11/1992 | European Pat. Off. . |
| 0 792 618 A1 | 9/1997 | European Pat. Off. . |
| 196 08 027 A1 | 9/1996 | Germany . |

OTHER PUBLICATIONS

G. Wagnières, Ch. Depeursinge, Ph. Monnier, M. Savary, P. Cornaz, A. Châtelain, H. van den Bergh; Photodetection Of Early Cancer By Laser Induced Fluorescence Of A Tumor–Selective Dye: Apparatus Design And Realization SPIE vol. 1203 Photodynamic Therapy: Mechanisms II (1990), pp. 43–52.

*Primary Examiner*—Marvin M. Lateef
*Assistant Examiner*—Shawna J Shaw
*Attorney, Agent, or Firm*—Akin, Gump, Strauss, Hauer & Feld, L.L.P.

[57] ABSTRACT

The diagnosis apparatus according to the invention for the picture providing recording of fluorescing biological tissue by way of an endoscope contains a stimulation light source which beams spectral components suitable for fluorescence stimulation into the tissue through the endoscope. The fluorescent light reflected by the tissue reaches through the endoscope optics into a head piece where it is split into a green, and spacially separated from this, a red spectral component and falls each on one half of a CCD solid body of a highly sensitive black and white camera. In an electronic and processor component the video signals allocated to the green and to the red spectral component are processed into two separate processing channels in a manner such that the separately processed green-red video signals are simultaneously inputted to a color video monitor and here may be superimposed to a red-green monitor picture, which may show changes of tissue indicating disease, for example dysplasia, carcinomas in situ etc., in all organs which are endoscopically accessible.

12 Claims, 3 Drawing Sheets

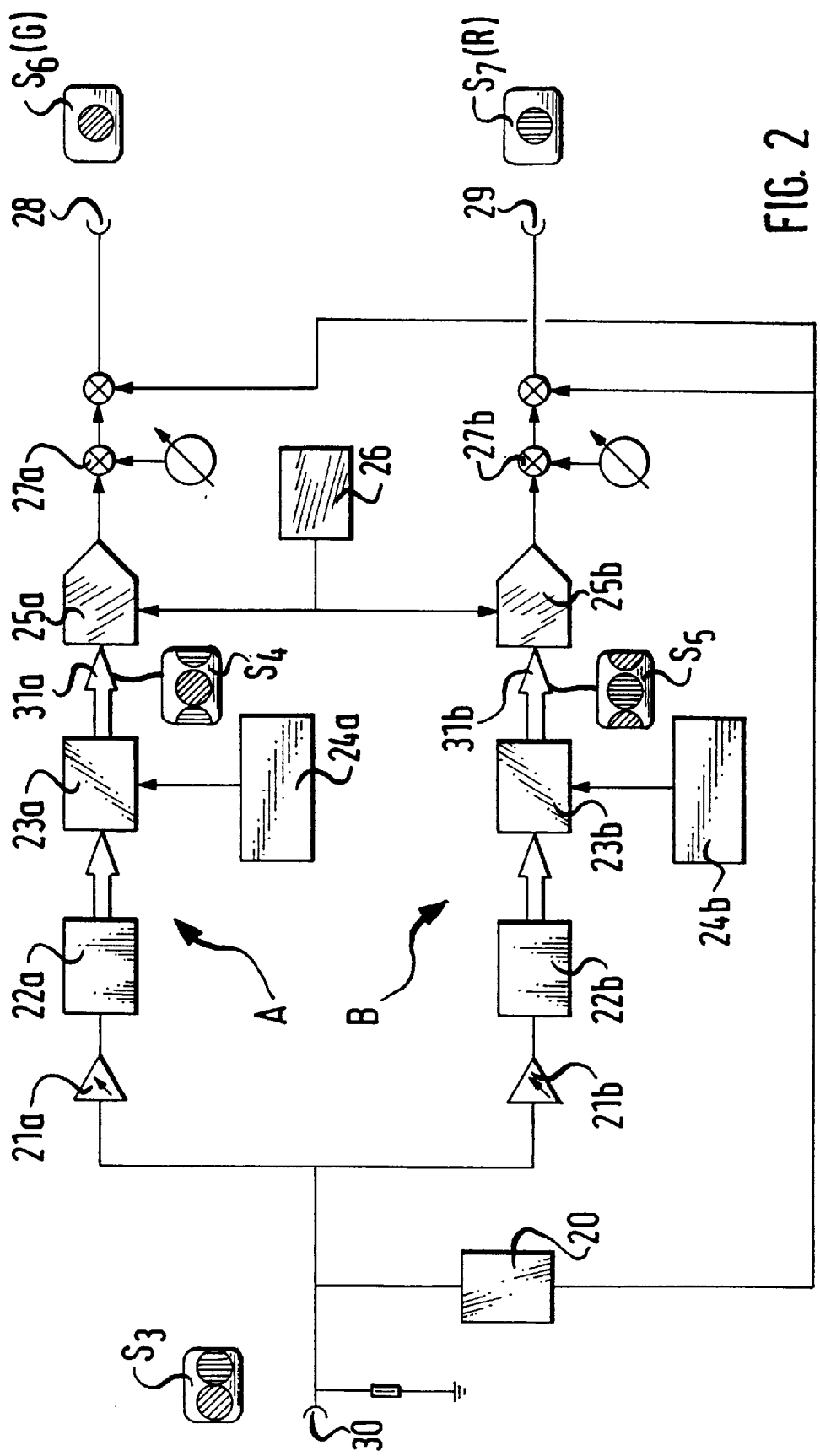

DIAGNOSIS APPARATUS FOR THE PICTURE PROVIDING RECORDING OF FLUORESCING BIOLOGICAL TISSUE REGIONS

BACKGROUND OF THE INVENTION

The invention relates to a diagnosis apparatus for the picture providing recording of fluorescing biological tissue regions, in particular by an endoscope with a light source which with the application of a filter arrangement emits at least one spectral region which is suitable for fluorescence stimulation in the tissue, with optics for acquiring and guiding the fluorescent light reflected by the tissue, with at least one video camera which records the pictures ot at least two various spectral regions of the fluorescence light reflected by the tissue and guided by the optics, and with picture processing means which by processing the picture information of the pictures recorded by the video camera of the various spectral regions according to a certain processing algorithm, produces in at least two separate channels in each case color-separate picture signals serving the diagnosis of the tissue region to be examined, wherein the color-separate picture signals at the outputs of the separate channels are inputted to an RGB color monitor so that this produces a mixed-color monitor picture.

With such a diagnosis apparatus (EP 0 792 618 A1) the light reflected by the tissue region examined is split into a red and green spectral region by way of a color splitter comprising a dichroitic mirror. The red spectral region is then separately from the green spectral region in each case recorded by an image intensified CCD solid-body camera. The analog output signals of the red and green video cameras after amplification and analog-digital conversion are led to a respective color channel of a video processor comprising a microcomputer. The digitalized picture signals are modified by the video processor with respect to the relative amplification of the digital video signals and upon this are converted back into analog picture signals, which simultaneously are supplied to a red and green input of a RGB color monitor which produces a phantom color photo in which healthy biological tissue appears cyanine colored and cancerous tissue red.

Further similarly constructed diagnosis apparatus for the picture providing recording of fluorescing biological tissue regions, in particular with the help of an endoscope are in each case described in EP 0 512 965 A1, U.S. Pat. No. 4,821,117, DE 196 08 027 A1 annd in SPIE Volume 1203 (1990), pages 43–52.

All previously mentioned diagnosis apparatus for the picture providing recording of fluorescing biological tissue function with two image-intensified cameras or CCD solid body pickups. Partly they also use a laser as a light source. Due to the double design of the video camera, the camera head to be fastened to the endoscope is correspondingly heavy and bulky and considerably hinders the handling of the endoscope.

BRIEF SUMMARY OF THE INVENTION

In view of the problems of the diagnosis apparatus known from the above mentioned state of the art it is the object of the invention to so form a diagnosis apparatus, that it is compatible with the known endoscopes and accessories, has a simple construction and small price, is very compact in particular with regard to the parts to be fastened to the endoscope, that its compromises the handling of the endoscope as little as possible and that a PC as a processing member can be done away with.

The diagnosis apparatus is to exploit the physical effect of the autofluorescence of biological tissue region and give a picture like representation of the observed tissue surface, so that it is possible to locate tumorous and pretumorous changes of tissue in an early as possible stage and to determine their extent. For this in particular belong dysplasia, carcinomas in situ and small papillary tumors which with conventional methods, for example endoscopic observation under white light, is quite difficult or even impossible to be able to recognize.

The diagnosis apparatus should also make do without a so-called photo sensitizer so that no special medication for fluorescence stimulation of the tissue must be enriched to the patient. Basically the system however can also operate with a suitable photo sensitizer.

One suitable diagnosis apparatus of the previously mentioned type which solves the above object is according to the invention characterized in that the video camera is a highly sensitive black and white CCD solid body camera and comprises a color splitter which disaggregates the at least two spectral regions of the received light into at least two spacially separated parallel picture regions allocated to the respective spectral region, on the black and white CCD solid body, and that the picture processing means time-sequencially receives the spacially separated picture regions on the CCD solid body and delays them against one another in separate channels such that at the outputs of the channels the previously separated color separate picture signals are simultaneously outputted.

Thus the basic principle of the diagnosis apparatus according to the invention lies in the spectral evaluation of the fluorescence information at least in the regions green and red with a single highly sensitive black and white camera or a black and white CCD solid body picture recorder instead of with two similar color video cameras. The employed black and white camera is considerably more sensitive that comparable color cameras and thus is suitable also for recording low-light fluorescence activities without an image intensifier. It can moreover integrate several pictures and thus further increase the light sensitivity. With the picture processing means according to the invention from the information of the black and white video camera a red-green picture may be represented on a conventional RGB video monitor. The respective color representation of the tissue region gives information on the condition of the tissue.

The color splitter of the solid body camera disaggregates the fluorescence picture of the recorded tissue region into a first picture region allocated to the color green and a second picture region spacially separated from this, which is allocated to the color red. Moreover the color splitter comprises a dichroitic mirror which reflects the red spectral region of the incident light and lets through the green spectral region. Furthermore in the color splitter there is provided a red filter which is arranged after the diacritic mirror and lies in the beam path of the red light.

Furthermore to the color splitter there belongs a mirror which reflects the incident light lying in the green spectral region. Finally allocated to the color splitter there is further allocated a green filter which is arranged after the mirror and lies in the beam path of the green light.

Of the two or more channels provided in the picture processor a first channel A is allocated to a green picture signal component and a second channel B to a red picture signal component, and the picture signal received in the first channel is after digitalization delayed by a delaying means by a first predetermined delay time, whilst the picture signal received in the second channel B after digitalization is delayed by a second delaying means by a second predetermined delay time which differs from the first delay time by about half a picture line. In this manner the output signals of both channels A and B, after the picture singals processed therein have been converted back into analog picture signals by way of a digital/analog converter and in each case the picture information disturbing and displaced with respect to time and allocated to the other color has been supressed in both channels by a blanking-out generator, the output signals of both channels A and B can be respectively supplied to the green and red input of the RGB color video monitor which produces the red-green picture.

In further embodiment forms the tissue may be stimulated with a special light source with more than one wavelength. Here in particular, an additional stimulation in the red spectral region is of interest. The red light which is dispersed back delivers a reflection picture which may be used for a quality improvement of the fluorescence picture. A simultaneous stimulation of the fluorescence with stimulation light in several spectral regions is also possible.

Fluorescence pictures with various stimulation spectrums may be gained simultaneously or after one another. From this again an individual picture may be deduced e.g. by superposition.

Instead of the two principly similar channels of the diagnosis apparatus according to the preferred embodiment form, the apparatus may comprise also more than two processing channels which are allocated to the respective color picture signals. Furthermore the diagnosis apparatus may additionally use the blue channel of the RGB video monitor, e.g. for the above mentioned reflection picture.

To directly accessible tissue surfaces such as e.g. the skin, outer sexual organs or the mouth cavity, the system is likewise applicable. In this case the endoscope may be done away with and where necessary instead of this a suitable lens system may be employed.

The light source is preferably equipped with a mercury-xenon lamp. Further a xenon lamp is also suitable. As for the rest the light source may also be formed by a laser or by at Least one diode laser.

A xenon lamp has at least in the visible region a relatively continuous spectrum which is why such a lamp is particularly suitable for white light representation in endoscopy. The spectrum of a mercury-vapour xenon lamp basically consists of that of a mercury-vapour lamp and that of a xenon lamp. With this in particular the maxima in the blue/violet region at 405 nm and 436 nm are of particular interest for the application with the diagnosis apparatus according to the invention, since with these wavelengths high powers are available for fluorescence stimulation. Other maxima of power of a mercury-vapour-xenon lamp, which possibly effect a disturbance on the white light picture and may result in a color falsification of the endoscope picture, where appropriate may be reduced or done away with by additional filters.

BRIEF DESCRIPTION OF THE DRAWINGS

Subsequently an embodiment example of the diagnosis apparatus according to the invention is described in more detail by way of the drawings. There are shown:

FIG. 2 as a block diagram the two channels A and B of the picture processing means and FIGS. 3a–c graphical picture signals as they occur on the CCD chip in FIG. 1 and in the two channels A and B of the picture processing means represented in FIG. 2.

DETAILED DESCRIPTION OF THE INVENTION

Figure 1:
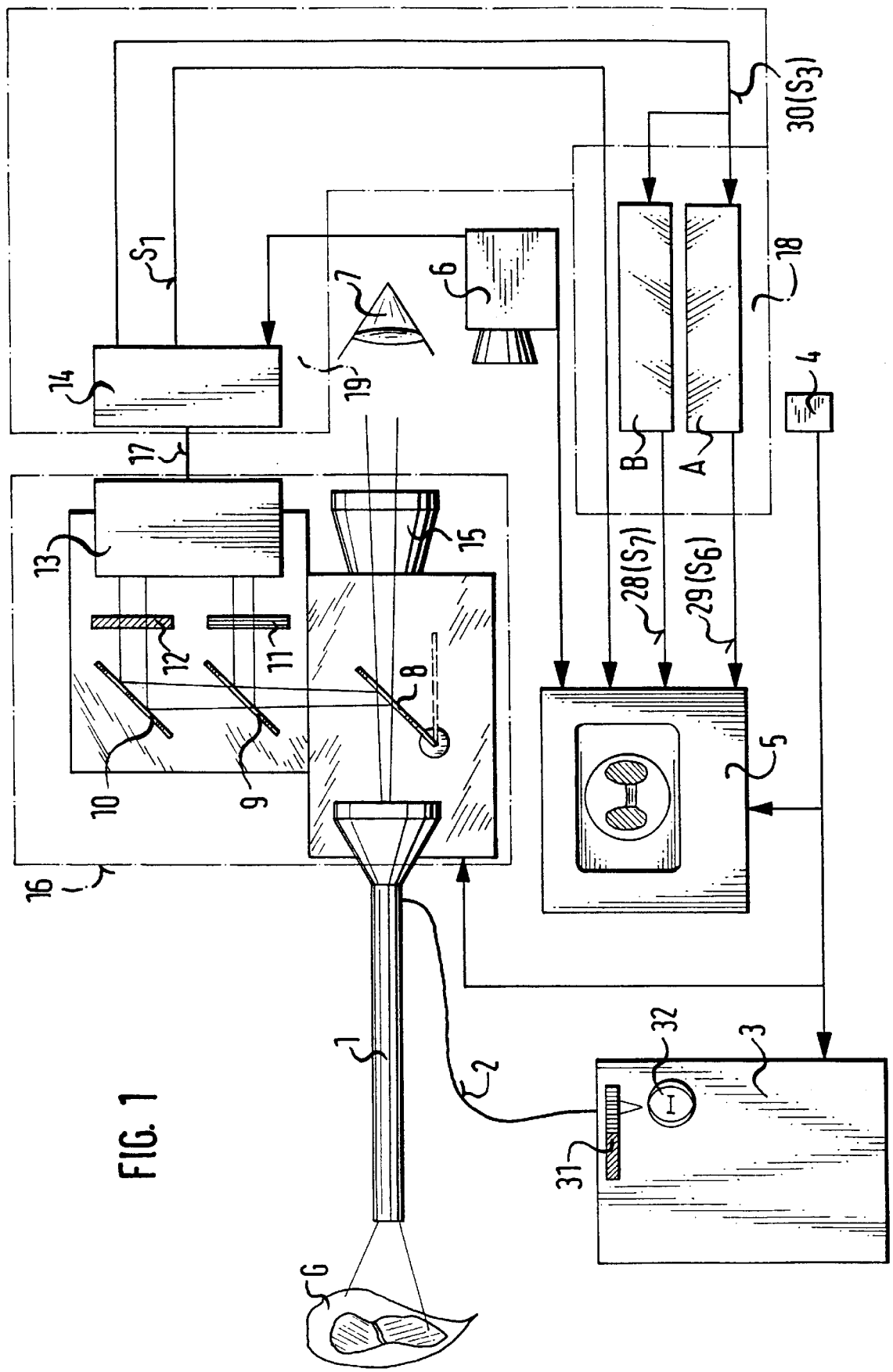
FIG. 1 a diagnosis apparatus in the form of schematic function blocks.

According to FIG. 1 in the known manner a light source 3 is connected to an endoscope via a fiber-optic 2 formed as a cable. The light source 3 contains a lamp, e.g. a mercury-vapour xenon lamp 32, and a filter 31 placed after this, which lets through a spectrum suitable for stimulating the fluorescence. The filter 31 on operating a switch 4 may be pivoted into and out of the beam path of the lamp 32. The switch 4 is located on the head piece 16 of the endoscope 1 or is designed as a foot switch.

In the pivoted-out condition of the filter 31, from the light source 33 white light for a conventional examination of a tissue region G, e.g. directly with the eye 7 is directly beamed into a fiber-optic located in the endoscope via the fiber-optic cable. In the pivoted-in condition of the filter 31 the light source 3 delivers, exiting the distal endoscope end, stimulation light for stimulating fluorescence in the tissue region G. Such fluorescence stimulating light lies preferably in the ultraviolet and/or blue spectral region. Instead of a single pivotable filter 31 also several filters may be pivoted to and fro, wherein a switch suitable for this and a filter drive are provided.

Onto the eyepiece part of the endoscope 1 the head piece 16 e.g. is attached with a suitable snap closure. The head piece 16 contains a folding mirror 8 which is synchronously pivotable with the filter 31 of the light source 3 into and out of the beam path of the light reflected by the tissue region G. The folding mirror 8 is pivoted out of the beam path given white light. In the fluorescence mode the picture providing light which is emitted from the tissue region G and received by the endoscope 1 reaches a dichroitic mirror 9 which for example reflects the red spectrum and lets through a green spectral component. Then the red spectral component firstly reaches a red filter 11 which improves the color separation, and afterwards reaches one half of a CCD solid body chip of a highly sensitive black and white CCD solid body camera. Parallel to this the green spectral component of the light gone through the diochroitic mirror 9, is deflected by a mirror 10 and reaches through a green filter 12 which improves the color separation to the other half of the CCD solid body chip 13. The head piece 16 contains further optical elements which are not shown, e.g. lenses. It may also contain a zoom lens which permits the picture size to be adapted to different endoscopes or tissue regions to he imaged.

The optics in the head piece 16 form a color beam splitter which disaggregates the two red green spectral regions of the received light into two spacially separate parallel picture regions allocated to the respective spectral region on the black and white solid body 13 of the camera.

The black and white camera applied is considerably more sensitive than comparable color cameras and thus is suitable for recording very weak light fluorescence activities without an image intensifier. It can furthermore integrate several pictures and thus further increase the light sensitivity.

The head piece 16 is connected to an electronics part 19 via a cable 17. This electronics part consists of camera electronics 14 and of a video procesor 18. The components of the electronic part 19 are e.g. accommodated in a relatively small table housing. The electronics part 19 comprises outputs Si, 28, 29 which are connected to a standardized RGB video monitor 5. The video monitor 5 delivers a red green picture of the tissue region G observed with the endoscope 1.

The head piece 16 further comprises an eyepiece 15 through which given white light, one may diagnose conventionally selectively with the eye or with an endoscopic color camera 6.

FIG. 2 shows the construction of a video processor 18. It comprises a standard video input 30 which is connected to an output of the camera electronics 14. A synchronous separator 20 separates the synchronizing impulse S1 of the video signal. Subsequently the input signal S3 is fed at the input in basically two identical channels A and B of which the channel A serves the processing of the imaging part allocated to the green spectral region, on the CCD solid body 13 and the channel B serves the processing of the imaging region allocated to the red spectral region on the CCD solid body 13.

In both channels A and B the input signal S3 is firstly amplified with amplifiers 21a, 21b and are coverted into a digital signal in anaolog-digital converters 22a, 22b. These digital signals then reach in each case a first-in first-out (FIFO) shifting register 23a and 23b respectively. The two FIFO registers 23a, 23b are respectively in connection with a delay generator 24a and 24b. The delay times of these two delay generators are set differently in both channels. The difference of the delay times corresponds to about half a picture line. The digitalized video signal is delayed in the FIFO register 23a of the first channel A by about a quarter line whilst the digitalized video signal in the second FIFO register 23b of the second channel B is delayed by about three quarters of a line. Subsequently the thus delayed video signals of both channels are converted again back into analog video signals in digital/analog converters 25a and 25b and in each case are subjected to an offset correction by correction members 27a and 27b.

At the circuit points 31a and 31b in front of the digital/analog converters 25a, 25b there are respectively present digital video signals S4 and S5 which are symbolically represented. With the digital video signal S4 the picture is displaced by a quarter line to the right and the green picture information is located in the center and is in each case neighbored by half a red picture component (cf. FIG. 3b). With the digital video signal S5 the picture is once again shifted to the right by half a line.

Figure 3A:
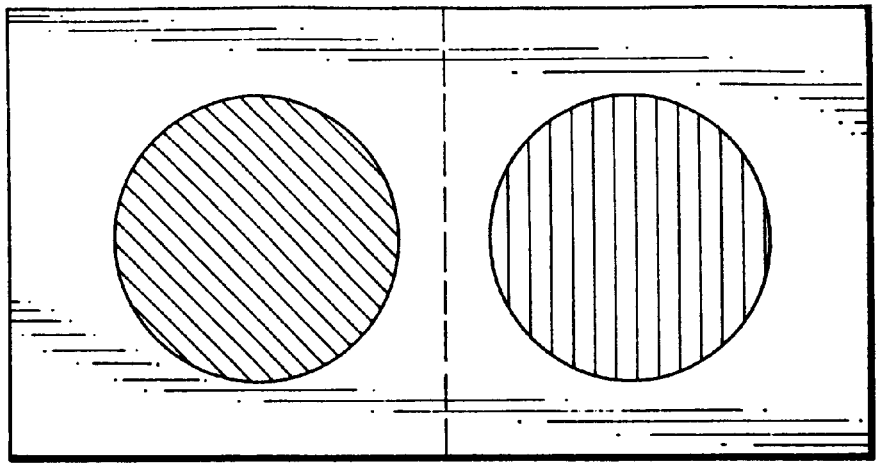
Figure 3B:
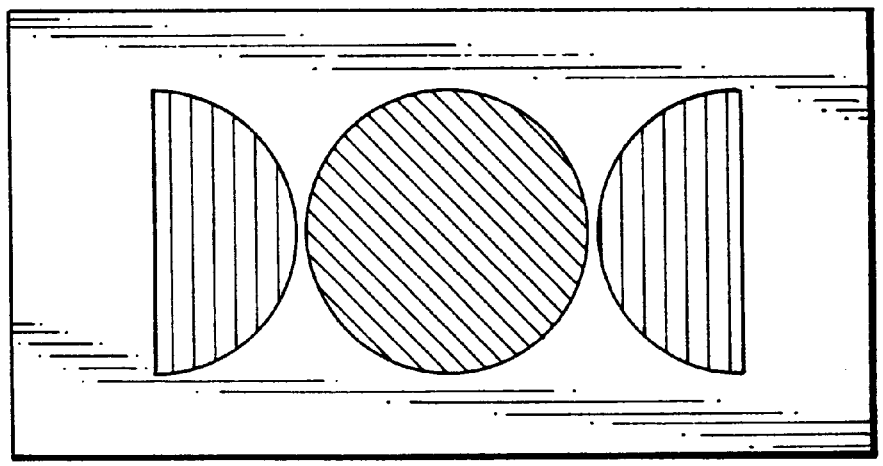
Figure 3C:
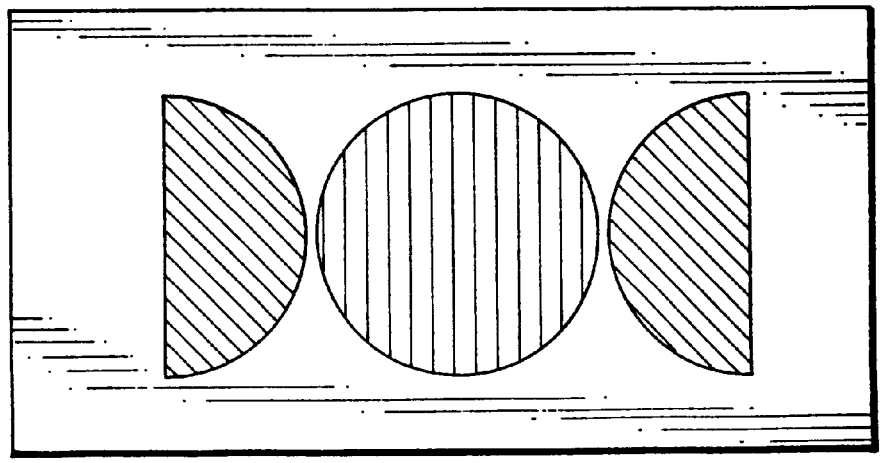

Here the red picture information is located in the center, neighbored by the two green frames (cf. FIG. 3c). FIG. 3a shows the picure as it falls on the CCD chip 13. A blanking generator 26 suppresses in both channels A and B the disturbing picture information of the other color. After the offset correction by the offset correction members 27a and 27b the synchronous impulse S1 is in each case mixed into the signal. At the output jacks 28 and 29 thus the green and red picture information S6 and S7 are respectively available. By connecting the output jacks 28 and 29 to the RGB input G "green" and R "red" respectively the color monitor 5 automatically produces a two-colored picture. To a video input a conventional color camera may also be connected in parallel.

At the two ouputs 28 and 29 of the picure processor 18 shown in FIG. 2 the two picture signals S6 according to the green picture information G and S7 according to the red picture information R thus appear simultaneously so that they may be shown superimposed on the color video monitor 5 without further ado.

The principle according to the invention may also be used with a stimulation of a tissue region with more than one wavelength. In particular also an additional stimulation in the red spectral region is conceivable. The red light dispersed back from the tissue region delivers a reflection image which for example may be applied to the blue connection B of the video color monitor.

Moreover a simultaneous stimulation of fluorescence light with several spectral regions is also possible. With this fluorescence pictures with several stimulation spectra may be obtained simultaneously or also after one another. From this again an individual picture may be deduced, e.g. by superposition. Finally the apparatus may also be equipped with more than two channels.

What is claimed is:

1. A diagnosis apparatus for picture recording of fluorescing biological tissue regions comprising:

a light source coupled to a filter arrangement for emitting at least one spectral region to effect fluorescence stimulation in tissue;

optics for receiving and guiding fluorescent light reflected by the tissue;

a video camera for recording pictures of at least two spectral regions of the fluorescence light reflected by the tissue and guided by the optics; and picture processing means for processing picture information of the pictures recorded by the video camera of the at least two spectral regions, and producing in at least two separate channels color-separate picture signals serving the diagnosis of the tissue region to be examined;

wherein the video camera comprises a single, highly sensitive, black and white CCD solid body camera and a color splitter for disaggregating the at least two spectral regions of the received light into a first picture region allocated to the color green and a second picture region spatially separated therefrom and allocated to the color to be received on the black and white CCD solid body camera;

the picture processing means time-sequentially receives the spatially separated picture regions on the CCD solid body camera and delays them against one another in separate channels such that the picture signals are simultaneously outputted and are inputted to an RGB color monitor to produce a mixed-color monitor picture.

2. A diagnosis apparatus according to claim 1, wherein the color splitter comprises a dichroic mirror which reflects the red spectral region and lets through the green spectral region.

3. A diagnosis apparatus according to claim 2, wherein the color splitter comprises a red filter arranged after the dichroic mirror in the beam path of the red light.

4. A diagnosis apparatus according to claim 1, wherein the color splitter comprises a mirror which reflects incident light in the green spectral region.

5. A diagnosis apparatus according to claim 4, wherein the color splitter comprises a green filter arranged after the mirror in the beam path of the green light.

6. A diagnosis apparatus according to claim 1, wherein the picture processing means comprise two basically similar channels of which the first channel is allocated to a green picture signal component and a second channel to a red picture signal component whereby the picture signal received in the first channel is digitized and delayed by a first predetermined delay time, and the picture signal received in the second channel is digitized and delayed by a second predetermined delay time which differs from the first delay time by about half a picture line.

7. A diagnosis apparatus according to claim 6, wherein the picture processing means comprises a digital/analog converter to convert the digital picture signals of both channels into analog picture signals, and a blanking generator in each of the two channels to suppress disturbing picture information displaced with respect to time and allocated to the other color.

8. A diagnosis apparatus according to claim 6, whereby the two color-separate picture signals are inputted to the green and red inputs of the RGB color monitor respectively.

9. A diagnosis apparatus according to claim 1, wherein the light source comprises a mercury-vapor xenon lamp.

10. A diagnosis apparatus according to claim 1, wherein the light source comprises a xenon lamp.

11. A diagnosis apparatus according to claim 1, wherein the light source comprises a laser.

12. A diagnosis apparatus according to claim 1, wherein the light source comprises at least one diode laser.

* * * * *